(12) United States Patent
Hansen et al.

(10) Patent No.: US 10,406,291 B2
(45) Date of Patent: Sep. 10, 2019

(54) AUTOINJECTOR HAVING NEEDLE SHIELD TRIGGERING

(71) Applicant: Novo Nordisk A/S, Bagsvaerd (DK)

(72) Inventors: Soeren Kjellerup Hansen, Fjenneslev (DK); Mads Schenstroem Stefansen, Copenhagen OE (DK); Matias Melander, Copenhagen (DK); Bastian Gaardsvig Kjeldsen, Hilleroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 33 days.

(21) Appl. No.: 15/301,108

(22) PCT Filed: Apr. 7, 2015

(86) PCT No.: PCT/EP2015/057526
§ 371 (c)(1),
(2) Date: Sep. 30, 2016

(87) PCT Pub. No.: WO2015/150578
PCT Pub. Date: Oct. 8, 2015

(65) Prior Publication Data
US 2017/0014575 A1    Jan. 19, 2017

(30) Foreign Application Priority Data
Apr. 4, 2014    (EP) .................................... 14163586

(51) Int. Cl.
*A61M 5/20* (2006.01)
*A61M 5/315* (2006.01)
(Continued)

(52) U.S. Cl.
CPC .......... *A61M 5/31501* (2013.01); *A61M 5/20* (2013.01); *A61M 5/24* (2013.01);
(Continued)

(58) Field of Classification Search
CPC ...... A61M 5/31501; A61M 5/20; A61M 5/24; A61M 5/31585; A61M 5/3234;
(Continued)

(56) References Cited

U.S. PATENT DOCUMENTS 2,752,918 A    7/1956   Uytenbogaar
5,658,259 A    8/1997   Pearson et al.
(Continued)

FOREIGN PATENT DOCUMENTS

WO    94/07553 A1    4/1994
WO    02/17996 A1    3/2002
(Continued)

*Primary Examiner* — Bradley J Osinski
*Assistant Examiner* — Nilay J Shah
(74) *Attorney, Agent, or Firm* — Wesley Nicolas

(57) ABSTRACT

An autoinjector (100) for expelling a single dose of drug from a drug cartridge (600) including a piston (630), the autoinjector including: a base (200, 220), a needle (500) that is fixedly mounted relative to the base (200, 220), a plunger (310, 320, 400) adapted for cooperation with the piston (630), an actuating spring (330) provided as a helical compression spring arranged to act on the plunger (310, 320, 400) by exerting an axial force on the plunger to drive the piston (630) distally, and a needle shield (350, 380) axially movable relative to the base (200, 220) between an extended position and a collapsed position. The autoinjector defines a lock (320, 328, 380, 388) that is released when the needle shield (350, 380) is moved from the extended position to the collapsed position. The lock (320, 328, 380, 388) releases to enable relative rotation between plunger thread (325) and base thread (205) causing release of the plunger (310, 320, 400) from the initial axial position and expelling the dose of the drug.

11 Claims, 7 Drawing Sheets

Figure 1A:
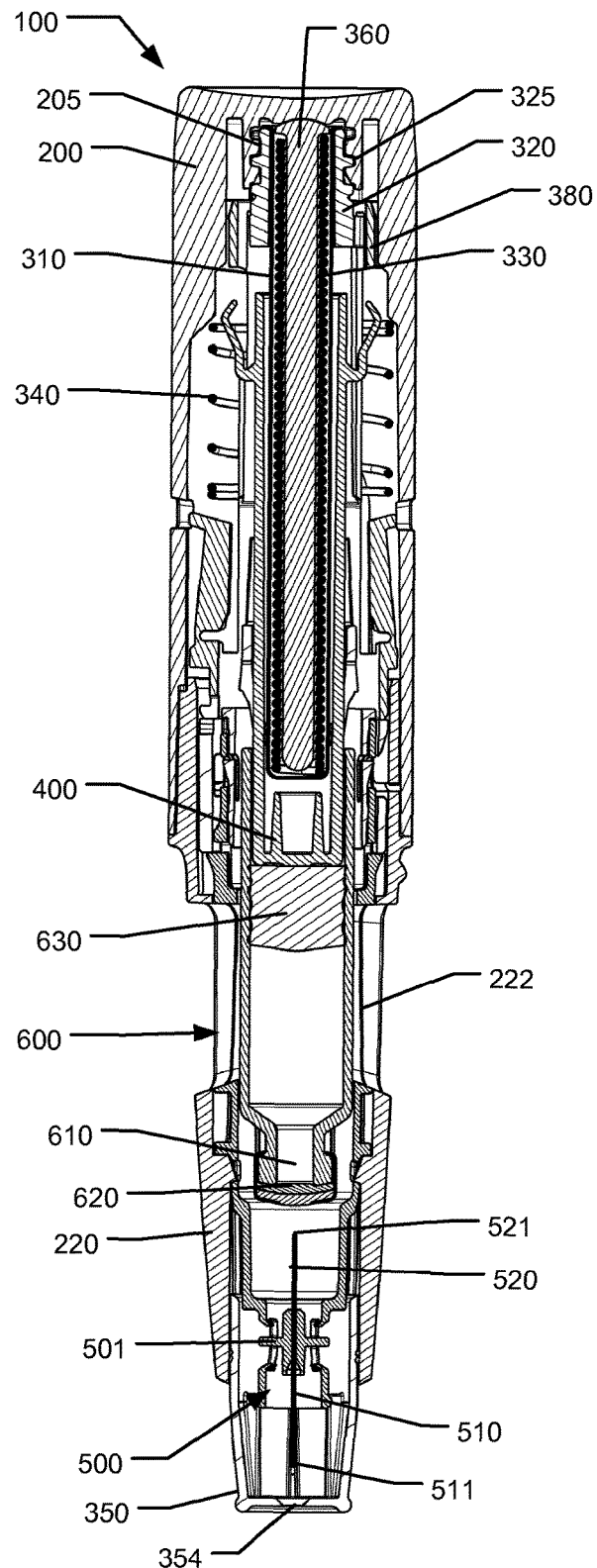

(51) Int. Cl.
*A61M 5/32* (2006.01)
*A61M 5/24* (2006.01)

(52) U.S. Cl.
CPC ...... *A61M 5/31585* (2013.01); *A61M 5/3234* (2013.01); *A61M 5/3243* (2013.01); *A61M 5/31565* (2013.01); *A61M 5/31583* (2013.01); *A61M 2005/2013* (2013.01); *A61M 2005/247* (2013.01); *A61M 2005/2433* (2013.01); *A61M 2005/3247* (2013.01)

(58) Field of Classification Search
CPC ............ A61M 5/3243; A61M 5/31565; A61M 5/31583; A61M 5/3159; A61M 5/31591; A61M 5/3232; A61M 5/3245; A61M 5/3257; A61M 5/326; A61M 5/31571; A61M 2005/2013; A61M 2005/2433; A61M 2005/247; A61M 2005/3247
See application file for complete search history.

(56) References Cited

U.S. PATENT DOCUMENTS

| | | |
|---|---|---|
| 6,210,369 B1 | 4/2001 | Wilmot et al. |
| 6,743,203 B1 | 6/2004 | Pickhard |
| 7,449,012 B2 | 11/2008 | Young et al. |
| 7,717,877 B2 | 5/2010 | Lavi et al. |
| 8,409,141 B2 | 4/2013 | Johansen et al. |
| 2005/0261634 A1* | 11/2005 | Karlsson ................. A61M 5/20 604/197 |
| 2013/0018313 A1 | 1/2013 | Kramer et al. |
| 2013/0274668 A1* | 10/2013 | Barrow-Williams ........................ A61M 5/2033 604/136 |
| 2013/0274676 A1 | 10/2013 | Ekman et al. |

FOREIGN PATENT DOCUMENTS

| | | |
|---|---|---|
| WO | 02/053214 A1 | 7/2002 |
| WO | 2004/028598 A1 | 4/2004 |
| WO | 2006/130098 A1 | 12/2006 |
| WO | 2008/116688 A1 | 10/2008 |
| WO | 2008116766 A1 | 10/2008 |
| WO | 2011/012903 A1 | 2/2011 |
| WO | 2011/101377 A1 | 8/2011 |
| WO | 2011/101382 A1 | 8/2011 |
| WO | 2011/111006 A2 | 9/2011 |
| WO | 2012/022810 A2 | 2/2012 |
| WO | 2012/085025 A1 | 6/2012 |
| WO | 2012/122643 A1 | 9/2012 |
| WO | 2012/173553 A1 | 12/2012 |
| WO | 2013/012745 A1 | 1/2013 |
| WO | 2014001319 A1 | 1/2014 |

* cited by examiner

AUTOINJECTOR HAVING NEEDLE SHIELD TRIGGERING

CROSS-REFERENCE TO RELATED APPLICATIONS

This application is a 35 U.S.C. § 371 National Stage application of International Application PCT/EP2015/057526 (published as WO2015/150578), filed Apr. 7, 2015, which claims priority to European Patent Application 14163586.2, filed Apr. 4, 2014; the contents of which are incorporated herein by reference.

FIELD OF THE INVENTION

The present invention relates to injection devices for injecting a medicament. In particular the present invention relates to autoinjector devices for injecting a medicament from a held cartridge and improvements relating to the performance of such injection devices.

BACKGROUND OF THE INVENTION

In relation to some diseases patients must inject a medicament on a regular basis such as once weekly, once daily or even a plurality of times each day. In order to help patients overcome fear of needles, fully automatic injection devices have been developed with the aim oft making the use of the injection device as simple as possible. Such devices are typically designed such that a user shall position the injection device onto the injection site and activate the device. Such activation causes the device to insert a needle into the skin, eject a dose of the medicament and subsequently move the needle into a shielded position.

Generally, for injection devices of the above type, main attention has been directed towards devices equipped with a glass cartridge where a needle cannula is fixedly attached to the outlet end of a cartridge. Such needle cannula is initially being covered in a sterile way by a cap member that during storage acts as a stopper for the needle cannula, and which requires removal prior to use. Typically, these devices further include a needle shield portion for shielding the needle before and/or after use. Disclosure of such devices is included in U.S. Pat. Nos. 7,449,012, 7,717,877 and WO2008/116688.

Some manufacturers prefer the type of cartridge having a pierceable septum which during storage provides a seal for the cartridge outlet and where the septum, upon use, is pierced by a needle cannula. Prior art devices using this type of cartridge are disclosed in U.S. Pat. Nos. 2,752,918, 5,658,259, 6,743,203, 6,210,369 and WO94/07553. Devices of that type hold a needle assembly and a cartridge in a separated storage configuration which upon activation of the device allows for subsequent connection to establish fluid communication between cartridge and needle assembly. In addition, automatic penetration of the needle into the skin of the user for subsequent automatic delivery of the medicament is typically incorporated.

While the above devices aim at providing a high level of automation, injection devices that provide automatic insertion of the needle into the dermis also prevent the user from controlling the insertion, which can lead to uneasiness for the user.

Injection devices that provide automatic delivery of the medicament, i.e. auto-injectors, typically use a drive spring as driving force for the injection. Before use, the drive spring will be held in a pre-tensioned position from which it is released upon activation of the device. After activation the drive spring uses the energy from the tension to drive forward the piston of a cartridge.

One problem associated with auto-injectors having needle shield operated triggering is that the release mechanism typically relies on at least one component that is exerted to excessive forces and that maintains the drivespring in a state where the plunger can be released for expelling the medicament of the cartridge. The triggering principle typically relies on at least one component that is deformed to unlock for releasing energy from the drive spring. Due to the excessive forces provided by the drive spring such principle often results in non-optimal performance of the needle shield movement.

Having regard to the above-identified prior art devices, it is an object of the present invention to provide an autoinjector that is improved regarding needle shield triggering by movement of a needle shield and which enables improved control of the device during operation.

Yet additional further objects of the invention are to provide measures for obtaining devices having a superior performance and, at the same time, enabling manufacture at a reduced cost.

BRIEF DESCRIPTION OF THE INVENTION

In a first aspect, the present invention relates to an autoinjector for expelling a single dose of drug from a held cartridge, comprising:
 a base,
 a drug cartridge arranged relative to the base, the cartridge comprising:
 a) an elongated body having a distal end and a proximal end and defining a central longitudinal axis, the body having a distally arranged outlet adapted for connection to a needle, and
 b) a piston accommodated in the body, the piston configured for being driven axially in the distal direction to expel a dose of a drug through the outlet,
 a plunger adapted for cooperation with the piston,
 an actuating spring arranged to act on the plunger to drive the piston distally,
 a needle shield axially movable relative to the base between an extended position and a collapsed position,
 wherein the autoinjector defines a lock configured for releasably maintaining the plunger in an initial axial position where the actuating spring is tensioned, the lock being operated by the needle shield,
 wherein the plunger defines a plunger thread and the base defines a base thread adapted to cooperate with the plunger thread,
 wherein prior to activation, a) the plunger thread engages the base thread and b) the lock acts to prevent relative rotation between the plunger and the base, thereby maintaining the plunger in the initial axial position, and
 wherein, upon the needle shield being moved towards the collapsed position, the lock is released to enable relative rotation between the plunger and the base causing release of the plunger from the initial axial position and expelling the dose of the drug.

In the autoinjector according to the first aspect, the device includes a needle shield triggered expelling assembly where a pre-stressed actuating spring is actuated for releasing axial movement of the plunger by a movement of the needle shield relative to the base. As the energy accumulated in the actuating spring is not changed when the needle shield is moved axially from the extended position to the collapsed position, the force exerted on the needle shield for performing this movement is not counteracted by the force exerted by the actuating spring.

In some embodiments, the base forms a housing of the device. In some embodiments, the autoinjector accommodates a needle that is fixedly mounted relative to the base. The needle comprises a front needle and may comprise a rear needle.

In some embodiments, the front needle is configured to be manually operable relative to the needle shield such that when the needle shield is held against an injection site, manual operation of the front needle relative to the needle shield or vice versa causes manual penetration of the front needle into the injection site and causes subsequent release of the lock. When the lock is released the autoinjector becomes triggered.

According to the first aspect of the invention, by configuring the device so that a pushing force exerted manually on a part of the device is transferred to a manual force acting on the needle for manual penetration of the front needle into the injection site, the user gains improved control of the insertion of the injection needle. At the same time, by using this configuration the needle is hidden from the user during an administration. By providing an improved control of the needle insertion procedure a potential uneasiness for the user can be alleviated. The first part of the activation movement moves the needle forward relative to the needle shield to insert the needle in the user's skin. The second part of the movement activates the expelling assembly. This allows the user to manually insert the needle before activating the device and an administration may be stopped in time should the user wish to abort the operation.

The needle may incorporate a sterility barrier either for the front needle, for the rear needle or for both. In some embodiments, the each of the sterility barriers may be formed as a flexible sheath configured as a closed cavity for accommodating at least a part of the respective ones of the front needle and the rear needle. The needle may from part of a needle assembly including a needle cannula having a front needle and a rear needle respectively protruding in the distal and proximal directions from a needle hub. The needle assembly may include front and rear covers forming sterility sheaths for the front needle and rear needle respectively. Each of the front and the rear covers may be formed as a rubber sheath which is penetrable by the pointed tip of the needle when the cover is forced towards the needle hub.

The injection device may comprise an actuator in the form of a stored energy source coupled to a drive ram and configured for driving the drive ram upon release of the lock. The energy source may be provided as a stored energy source, such as an actuating spring or a pre-strained spring, a compressed gas etc. In other forms, the energy source is configured to become charged during an initial operation of the device prior to activation of the injection mechanism.

In particular forms, the actuator is provided as a helical compression spring that exerts an axial force on the plunger. The plunger may include a drive ram and a spacing member positioned between the drive ram and the piston of the held cartridge.

In some embodiments the autoinjector may include a needle shield spring which is associated with the needle shield and the needle to urge the front needle into its shielded state or to urge the needle shield into the state where the front needle is shielded. In some embodiments the needle shield spring is an element separate from the actuator or the actuating spring.

In some embodiments of the autoinjector, the lock includes a first lock element that is axially movable as the needle shield moves from the extended position towards the collapsed position. The first lock element and the plunger define respective cooperating lock geometries configured to, prior to activation, maintain a rotational lock between the plunger and the base, the cooperating lock geometries being adapted to unlock to enable rotation between the plunger and base upon the needle shield being moved towards the collapsed position.

In some embodiments of the autoinjector, the first lock element is prevented from rotating relative to the base and wherein the lock element and the plunger define respective cooperating lock geometries configured to, prior to activation, maintain a rotational lock between the plunger and the lock element, the cooperating lock geometries being adapted to unlock to enable rotation between the plunger and the lock element upon the needle shield being moved towards the collapsed position.

In some embodiments of the autoinjector the base thread is fixedly associated with the base.

In some embodiments the lock element defines a first lock feature and the plunger defines a cooperating lock feature, wherein one of the first lock feature and the cooperating lock feature defines an axial track and wherein the other of the first lock feature and the cooperating lock feature defines a track follower. In such embodiment the axial track may be formed as a track that extends in a direction parallel with the central longitudinal axis.

Hence, when the needle shield is moved from the extended position towards the collapsed position, the lock is released without inducing a relative rotation between the lock element and the plunger.

In some embodiments of the autoinjector the base thread is defined by a rotatable component that is axially fixed but rotatable mounted relative to the base, wherein the plunger thread is prevented from rotating relative to the base, wherein the lock includes a first lock element that is axially movable as the needle shield moves from the extended position towards the collapsed position, wherein the lock element and the rotatable component define respective cooperating lock geometries configured to, prior to activation, maintain a rotational lock between the rotatable component and the base, the cooperating lock geometries being adapted to unlock to enable rotation between the rotatable component and the base upon the needle shield being moved towards the collapsed position.

In some embodiments of the autoinjector the first lock element is prevented from rotating relative to the base and wherein the lock element and the rotatable component define respective cooperating lock geometries configured, prior to activation, maintain a rotational lock between the rotatable component and the lock element, the cooperating lock geometries being adapted to unlock to enable rotation between the rotatable component and the lock element upon the needle shield being moved towards the collapsed position.

In some embodiments of the autoinjector the plunger thread is rotationally fixed relative to the plunger and the plunger is rotationally fixed relative to the base.

In some embodiments of the autoinjector the plunger thread is engaged with the base thread during an initial first axial displacement of the plunger and where the plunger thread is released from engagement with the base thread allowing the plunger to subsequently continue axial displacement in a second axial displacement.

In some embodiments of the autoinjector an external diameter of the plunger thread is larger than the internal diameter of a cylindrical section of the cartridge.

In some embodiments of the autoinjector the plunger thread is accommodated at the proximal end of the plunger.

In some embodiments of the autoinjector the actuating spring is a helical compression spring arranged internally in a longitudinal bore of the plunger.

In some embodiments of the autoinjector the device irreplaceably accommodates a cartridge within the base and wherein the cartridge cannot be removed from the device without the use of tools.

In some embodiments of the autoinjector the force acting for causing rotation between the plunger and the base for releasing the plunger from the initial axial position is at least partly exerted by the actuating spring.

In some embodiments, the force acting for causing rotation between the plunger and the base for releasing the plunger from the initial axial position is exclusively exerted by the actuating spring.

In some embodiments, an externally applied force on the needle shield for causing the needle shield to be moved into the collapsed position is not transmitted into a force component acting to cause rotation between the plunger and the base for releasing the plunger from the initial axial position.

The cartridge body may define a proximally facing rear surface. The distally arranged outlet of the cartridge may comprise a pierceable septum adapted to be pierced by the rear needle of a needle assembly having both a front needle extending in the distal direction and a rear needle extending in the proximal direction. In alternative configurations, the cartridge body outlet portion includes an injection needle fixedly attached relative to the cartridge body.

In some embodiments, the actuator may be capable, upon release of the lock, to cause the cartridge and the rear needle to enter into the state where the cartridge septum is pierced by the rear needle and subsequently to cause the drive ram to move to dispense the medicament through the needle.

The injection device may incorporate an activator which is mechanically associated with the needle so that when the activator and the needle shield is moved relative to each other it causes the front needle and the needle shield to move relative to each other. In some embodiments the needle substantially follows movement of the activator as the activator moves relative to the needle shield.

In some embodiments the activator is configured to define a housing section which at least partly accommodates the cartridge and where the housing section is adapted to be gripped by the hand of the user. In such embodiment, the activator may be coupled to the needle to transfer a force from the activator to the needle when the activator is moved relative to the needle shield.

As used herein, the term "medicament" is meant to encompass any medicament-containing flowable drug capable of being passed through a delivery means such as a hollow needle or cannula in a controlled manner, such as a liquid, solution, gel or fine suspension. Also lyophilized drugs which prior to administration are dissolved into a liquid form is encompassed by the above definition. Representative medicaments includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

DETAILED DESCRIPTION OF THE INVENTION

Figure 1B:
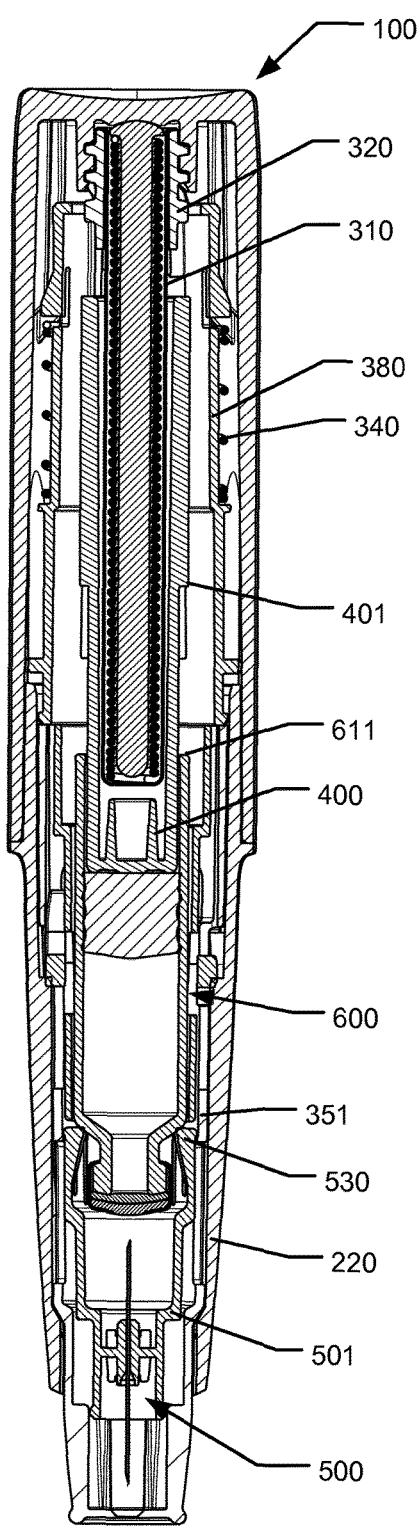
Figure 2A:
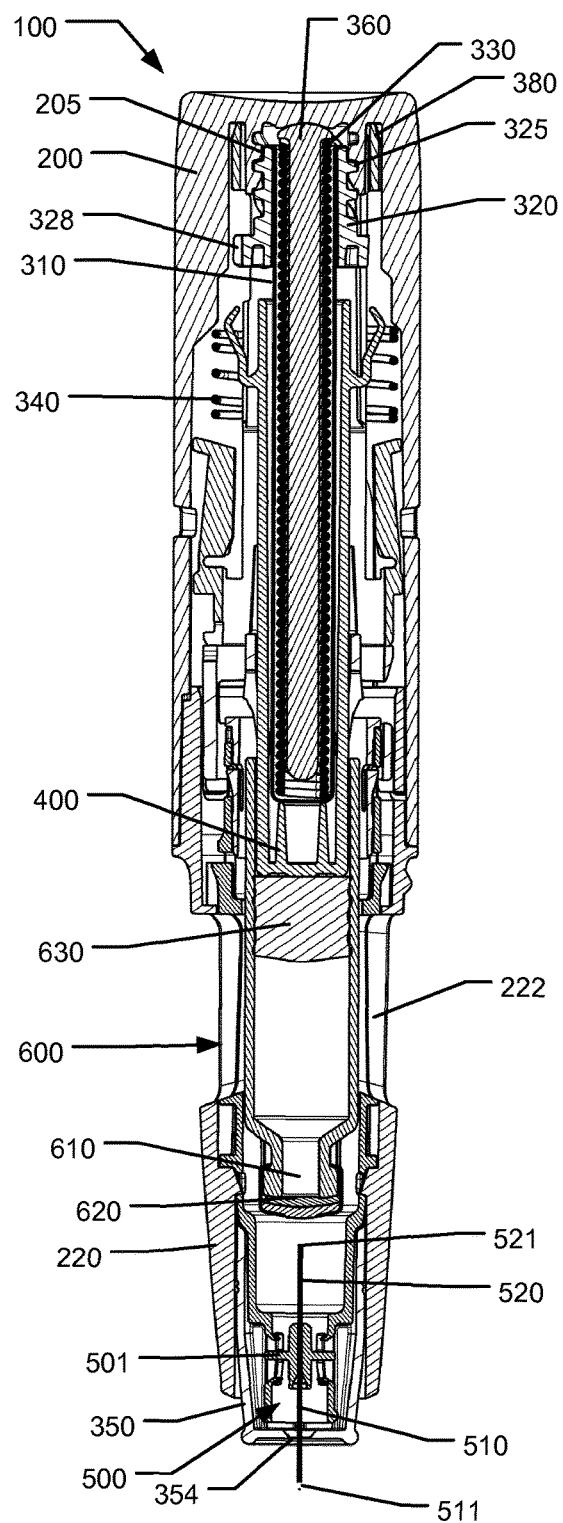
Figure 2B:
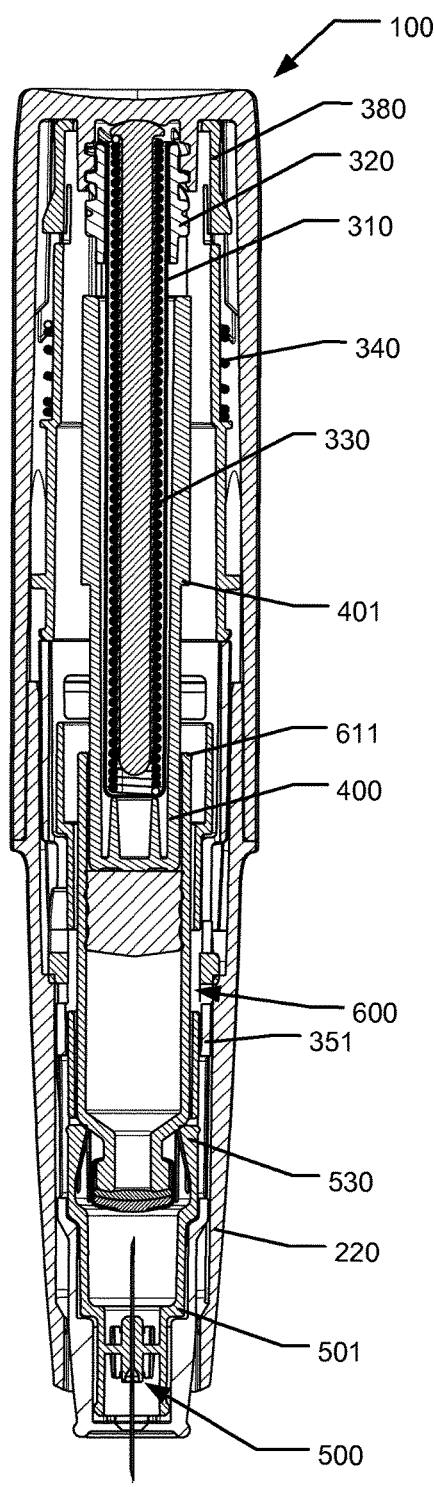
Figure 3A:
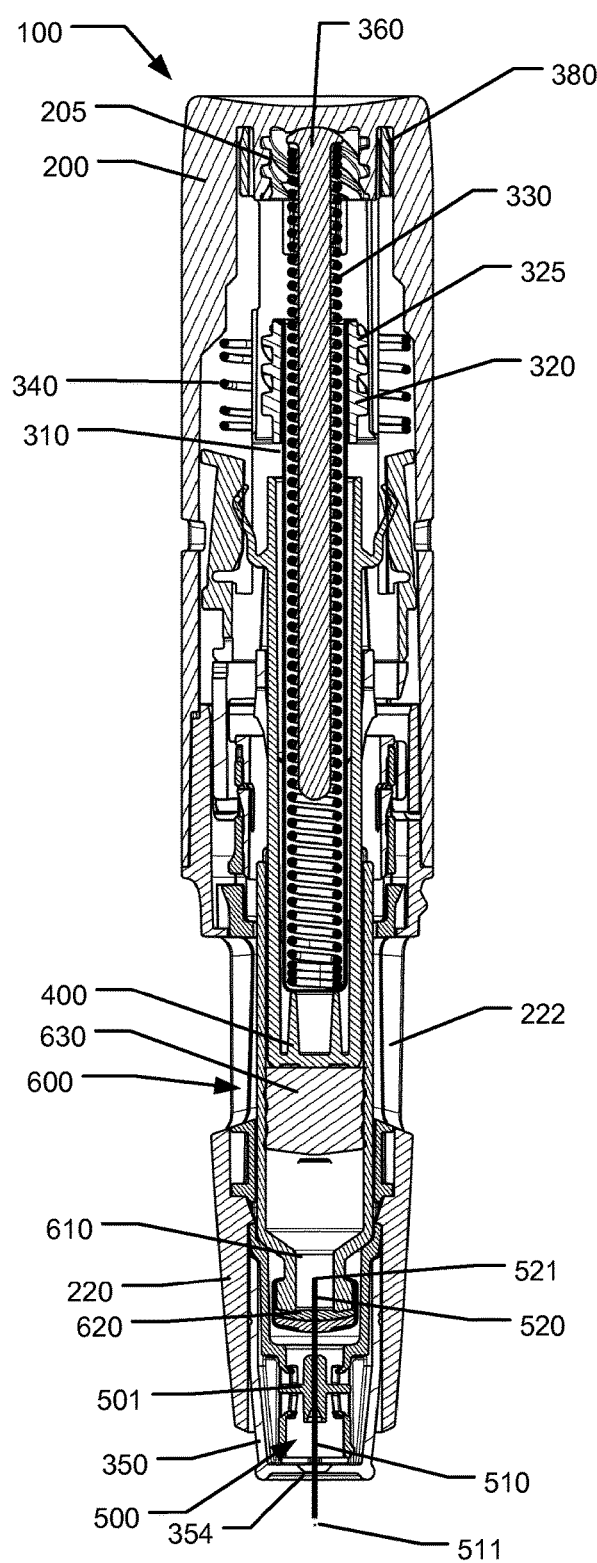
Figure 3B:
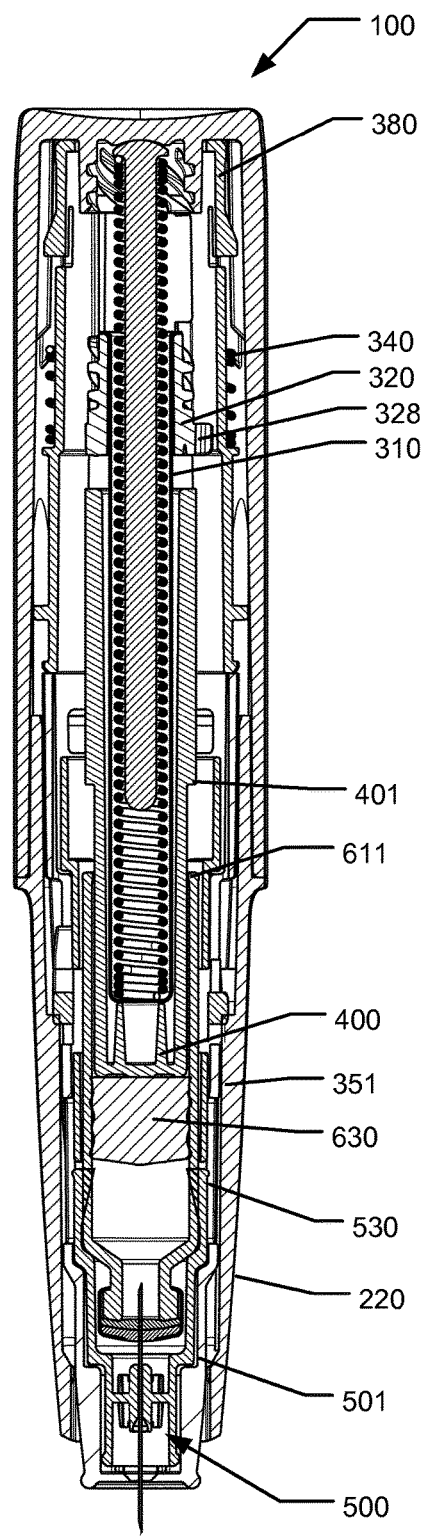
Figure 4A:
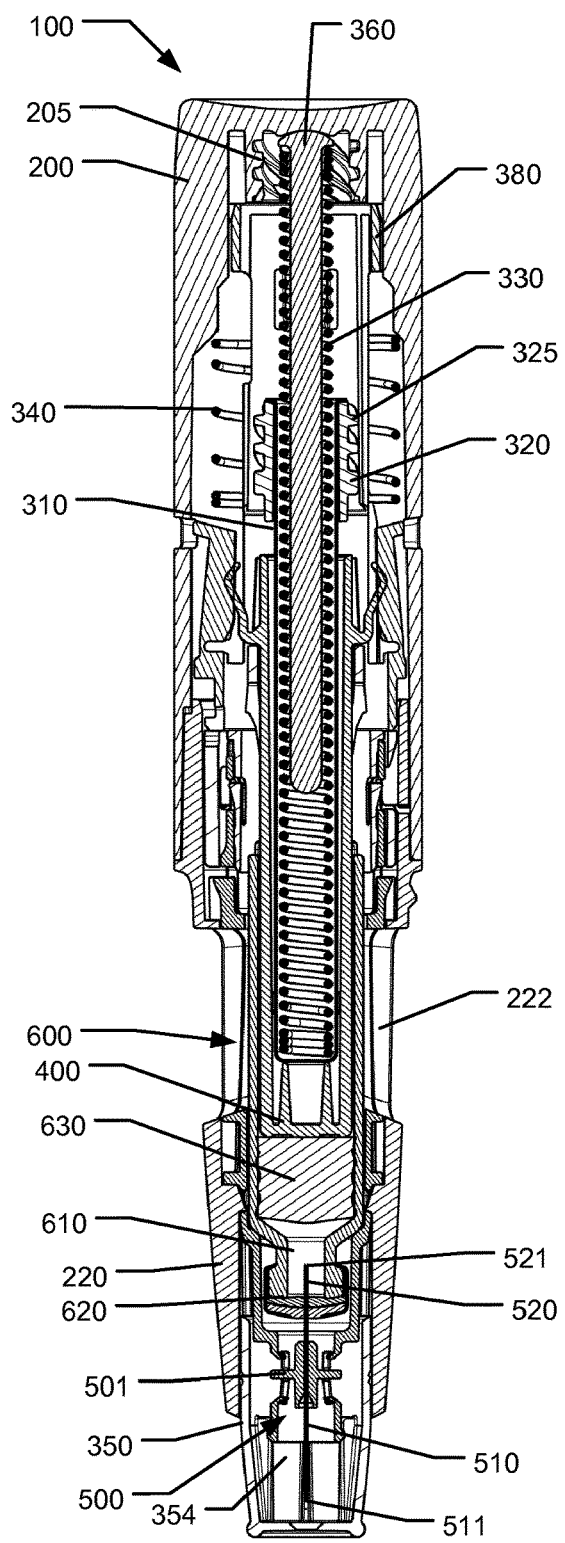
Figure 4B:
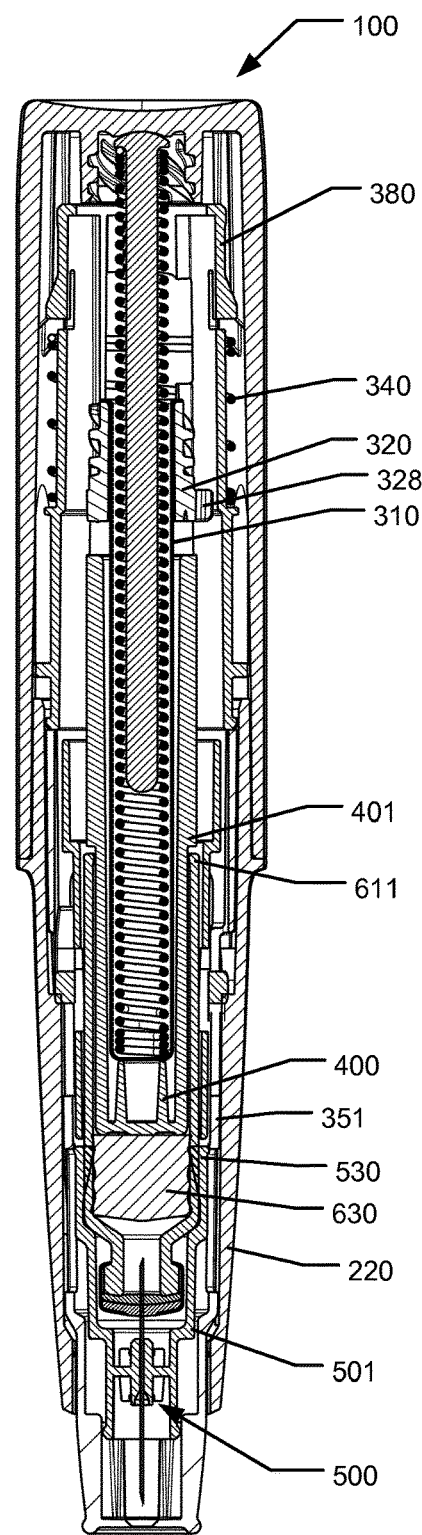
Figure 5:
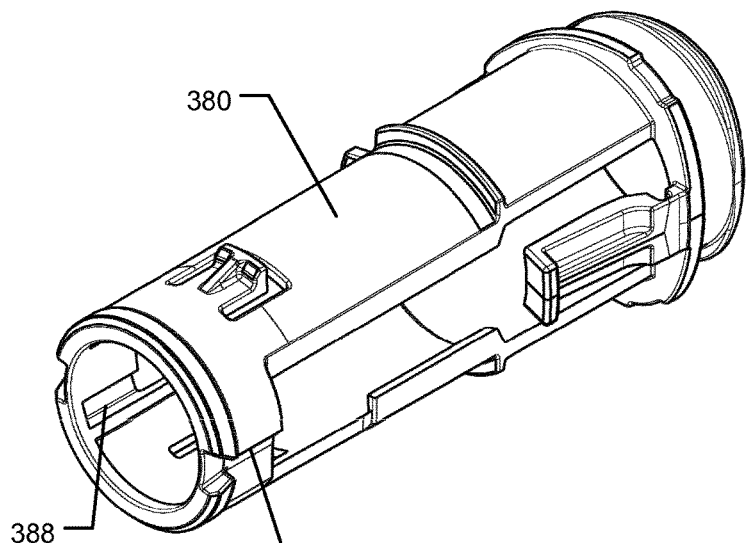
Figure 6:
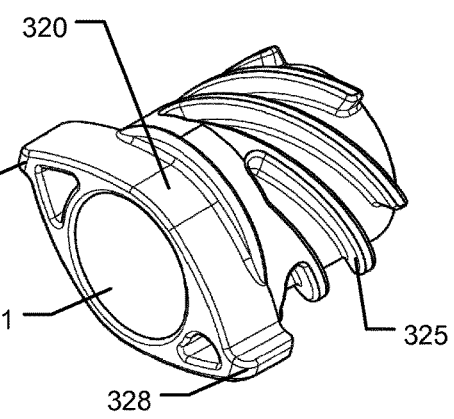
Figure 7:
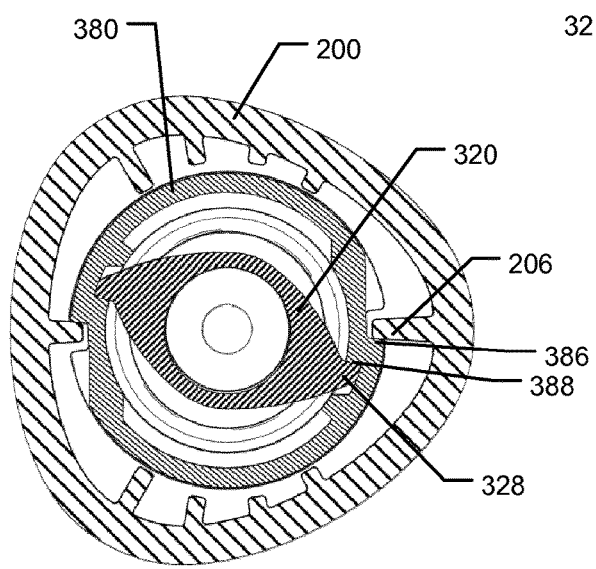
Figure 8A:
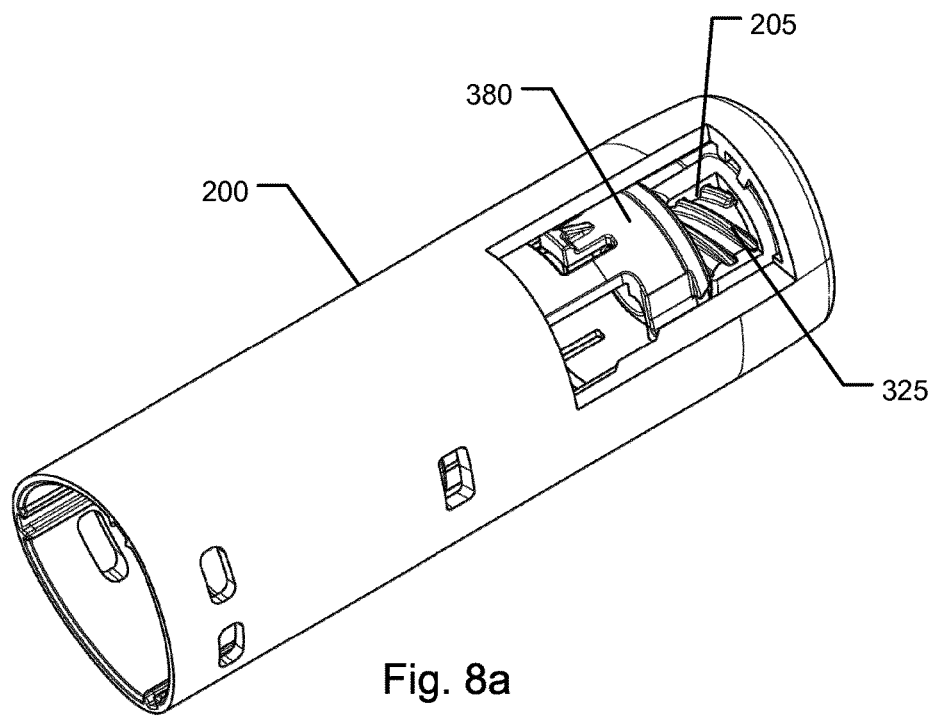
Figure 8B:
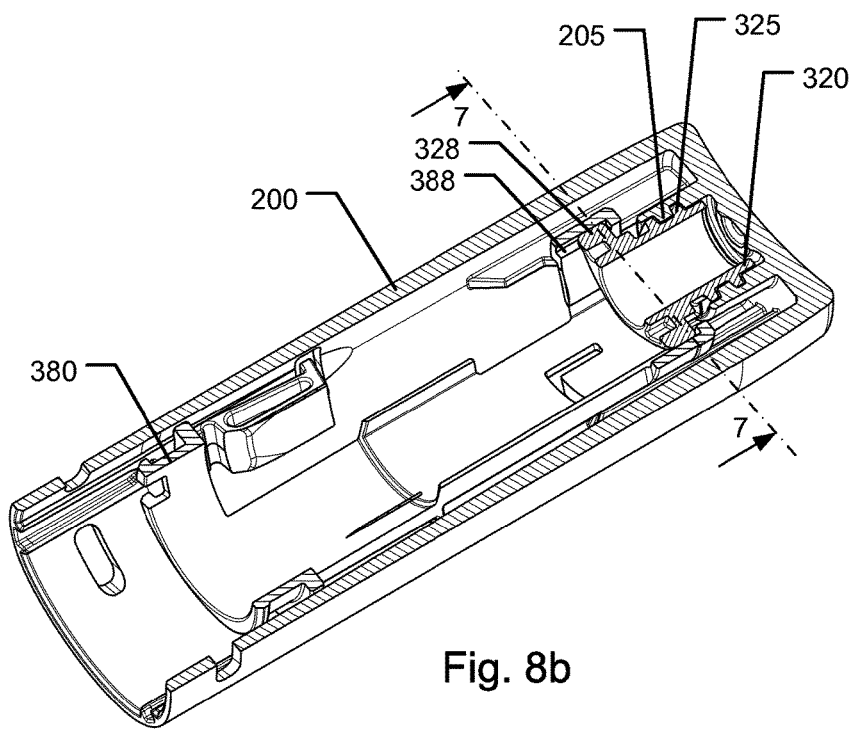
Figure 9:
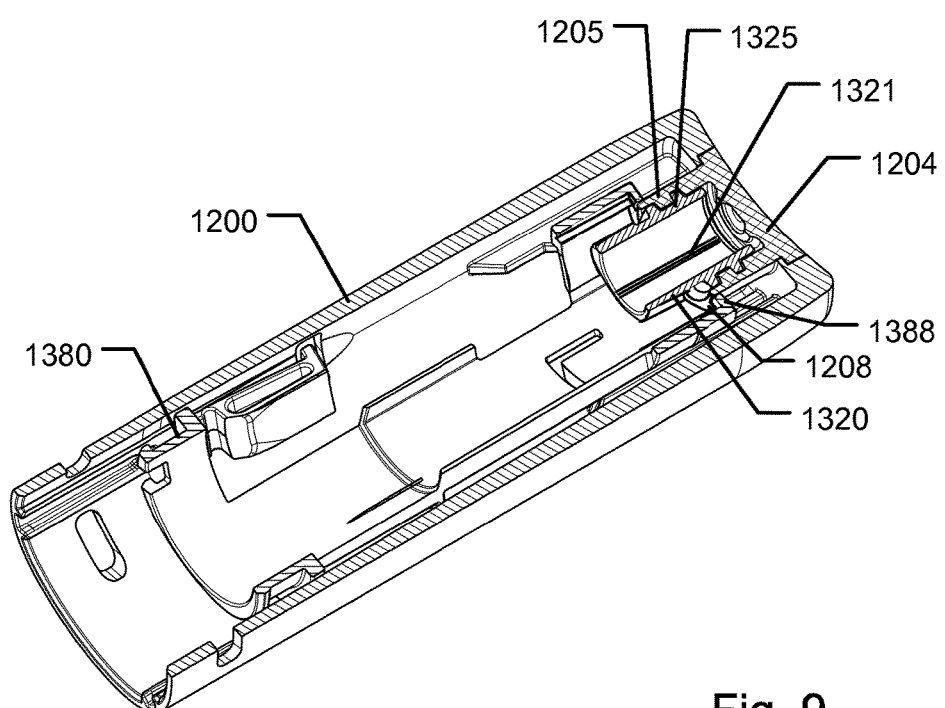

The invention will now be described in further detail with reference to the drawings in which:

FIGS. 1a and 1b shows sectional front and side views of an exemplary embodiment of a first type injection device 100 according to the invention, the injection device being in an initial shielded state, FIGS. 2a and 2b shows sectional front and side views of the device 100 illustrating a state where a front needle fully protrudes from a needle shield, FIGS. 3a and 3b shows sectional front and side views of the device 100 illustrating a state where the cartridge has been connected to the needle for fluid delivery and wherein expelling has been initiated, FIGS. 4a and 4b shows sectional front and side views of the device 100 illustrating a state where a predetermined dose of medicament from the cartridge has been expelled and the needle shield has returned to the shielded state, FIG. 5 is a detailed perspective view of a trigger element of the device 100, FIG. 6 is a detailed perspective sectional view of a release nut of the device 100, FIG. 7 shows a cross sectional view of a release nut assembly of the injection device 100, FIG. 8a is a partly cut perspective view of a top housing section of the injection device 100, FIG. 8b is a cross sectional perspective view of the release nut assembly of the injection device 100, and FIG. 9 shows a schematic representation of the main components for an alternative trigger release mechanism of an autoinjector of a second type.

The following is a description of an exemplary embodiment of a medical injection device 100 for administering a pre-determined amount of a liquid medicament. FIGS. 1a through 4b show various states of the injection device 100 during operation thereof with different views offering a detailed assessment of the operating principles.

Injection device 100 includes a generally tubular housing that extends along a central longitudinal axis. The housing forms a base that includes a lower housing section 220 arranged at a distal end of the device and a top housing section 200 arranged at a proximal end of the device. The lower housing section 220 and the top housing section 200 are joined to each other to form an enclosure to accommodate a medicament cartridge 600.

Injection device 100 may further include a removable protective cap (not shown) that attaches to a distal end of the device 100 to protect a needle end of the device 100. The lower housing section 220 includes two opposing windows 222. When the cap has been removed from the device 100, the windows 222 allow visual inspection of the medicament contained within the device 100. In addition, windows 222 allow a user of the device to determine whether or not the device 100 has been used for an injection by inspecting the presence or the location of a piston of a medicament cartridge 600 arranged within the housing. In the shown embodiment top housing section 200 is for manufacturing reasons formed as an element separate from but permanently fixed to lower housing section 220 but may in alternative embodiments be formed integral with lower housing section 220.

FIGS. 1a and 1b show front and side sectional views of the device 100 after the protective cap has been removed but in a condition prior to the administration operation. Shown protruding from the distal end of the lower housing section 220 is a needle shield 350 which is arranged coaxially and slidable relative to lower housing section 220. Needle shield 350 is slidable relative to the housing between a distal extended position where a front end of a needle assembly 500 arranged internally in lower housing section 220 is in a shielded state and a second proximal collapsed position where a front needle end of the needle assembly 500 protrudes through an aperture 354 arranged in the central part of a distal wall surface of the needle shield 350.

The injection device 100 is configured for being triggered to inject a dose when the needle shield 350 is moved from the distal extended position towards the collapsed position. The protective cap, when attached to the lower housing section 220, prevents the needle shield 350 from being manipulated and thereby prevents premature triggering of the injection device 100.

Lower housing section 220 accommodates a medicament filled cartridge 600 having an outlet 610 covered by a cartridge septum 620 adapted to be pierced by a needle for establishing fluid communication with the cartridge interior and having a slidably arranged piston 630. Piston 630 is driveable towards the outlet 610 when a needle pierces the cartridge septum 620 in order to dispense medicament from the cartridge 600. The dispensing is controlled by an expelling assembly. Cartridge 600 is arranged movable with respect to the lower housing section 220 from a proximal storage position to a distal active position.

Distally in the lower housing section 220 is a needle unit in the form of a needle assembly 500 arranged in an initially separated configuration with respect to cartridge 600. In the shown embodiment, needle assembly 500 includes a needle cannula having a front needle 510 and a rear needle 520 respectively protruding in the distal and proximal directions from a needle hub 501. Both front needle 510 and rear needle 520 include pointed tips 511 and 521 for respectively piercing the skin of a user and the cartridge septum 620.

Although not shown in the figures, the needle assembly 500 furthermore may include front and rear covers forming sterility sheaths for the front needle 510 and rear needle 520 respectively. Each of the front and the rear covers may be formed as a rubber sheath which is penetrable by the pointed tip of the needle 511/521 when the cover is forced towards the needle hub 501. Prior to use of the device, each of the two covers assumes the extended position in which the cover seals of the respective one of the front 510 and rear needle 520. The front and rear covers may be attached to the hub 501 either by gluing, welding, interference fit, a separate mounting element, or similar.

The needle cannula may be attached to the hub 501 by gluing, interference fit or similar joining process. In the embodiment shown, the hub 501 is an element separate from the housing but may in alternative embodiments be formed as a part of the housing 200/220. Hub 501 is formed as a generally tubular structure which extends proximally along the cartridge and even further to a position proximal to the cartridge. In this way the hub 501 supports the cartridge 600 along an exterior cylindrical wall of the cartridge. As such, the hub 501 is designed to perform as a cartridge holder relative to which the cartridge 600 is allowed to axially slide between the proximal storage position and into the distal active position.

In the shown embodiment, the needle hub 501 and hence the needle cannula is axially mounted relative to the housing of the device 100 so that the needle cannula follows axial movements of the housing when the housing is moved relative to the needle shield 350.

In the shown embodiment, the needle shield 350 is formed as a generally tubular member having a distal face arranged to initially cover the front needle 510. The needle shield 350 is mounted slidable relative to the lower housing section 220 allowing limited axial movement by a predefined axial distance.

The needle shield 350 cooperates with a trigger element 380 which is located proximally to the needle shield 350. Trigger element 380 is also formed as a generally tubular element and extends axially in the proximally direction from the needle shield to a location close to the proximal end of top housing section 200. In the assembled state of the device 100, the needle shield 350 and the trigger element 380 perform as a single entity, i.e. the movement of trigger element 380 follows axial movement of the needle shield 350. Hence the trigger element 380 is movable from a distal position corresponding to the extended position of the needle shield 350 to a proximal position corresponding to the collapsed position of the needle shield 350. In the shown embodiment, each of the needle shield 350 and the trigger element 380 are mounted in a way that prevents rotational movement relative to the housing 200/220.

The trigger element 380 is urged in the distal direction by means of shield spring 340 so that when no external applied force is exerted on the needle shield, the needle shield assumes its distal extended position which is shown in FIGS. 1a and 1b. In this position a stop geometry on trigger element 380 and/or needle shield 350 prevents the two components from moving further in the distal direction. When an externally applied force is exerted on the needle shield 350 for moving the needle shield in the proximal direction relative to the housing, such as when device 100 is pressed with the needle shield against an injection site, the externally applied force acts counter to the force provided by the needle shield spring 340 resulting in the needle shield 350 and the trigger element 380 being forced to move in the proximal direction. When the needle shield 350 assumes the proximal collapsed position a proximal end surface of the trigger element 380 prevents the trigger element and the needle shield 350 from moving further proximally relative to the housing (cf. FIGS. 2a and 2b).

As the device 100 is removed from the injection site, the needle shield 350 will move distally due to the force from the shield spring 340. After an injection has been performed, as the needle shield 350 reaches its distal position again, as shown in FIGS. 4a and 4b, it will be locked in this position to render the needle shield inoperable (to be further explained below).

The needle assembly 500 is arranged at the distal end of the lower housing section 220, such that the needle shield 350 completely covers the needle assembly when the needle shield is in its extended position. When the needle shield 350 is in its proximal collapsed position, the front needle 510 protrudes through the aperture 354 of needle shield 350.

As indicated in FIG. 1b, the cartridge 600 is maintained in its proximal storage position by means of two resilient arms 530 that extend radially inwardly from the needle hub 501. In the initial state shown in FIG. 1b, the resilient arms 530 assume a position where they support and retain a neck portion of the cartridge 600 to prevent the cartridge from moving in the distal direction. The resilient arms 530 are adapted to flex radially outwards when sufficient force acting to move the cartridge 600 in the distal active position is exerted on cartridge 600. However, in the initial state where the needle shield 350 assumes its distal extended position, a blocking geometry 351 of the needle shield 350 encircles the resilient arms 530 to prevent them from flexing outwards and thus prevents the cartridge 600 from being moved distally. As will be described later, the blocking geometry 351 is configured to move axially when the needle shield 350 is moved into its proximal collapsed position making room for the resilient arms 530 to be flexed radially outwards.

The expelling assembly of injection device 100 is based on a plunger device that is driven in the distal direction along the central longitudinal axis of the device for advancing the piston 630 to thereby expel a dose from the cartridge 600. The plunger device in the shown embodiment includes a drive ram 310 and a spacer member 400. In device 100 an actuator 330 is arranged in the proximal part of the device providing a stored energy source for exerting a distally directed force on drive ram 310. Spacer member 400 is a generally tubular member that is positioned between drive ram 310 and the piston 630 of the cartridge 600. Spacer member 400 acts as an intermediary member for transferring a force exerted by the drive ram 310 on the piston 630 for forwarding the piston in the distal direction.

The actuator is provided in the form of actuating spring 330 that in the shown embodiment is provided as a pre-stressed helical compression spring. The actuating spring 330 is energized by straining the compression spring during manufacture of the device. The drive ram 310 is furthermore hollow to allow the actuating spring 330 to be positioned within the drive ram 310. A guiding element 360 arranged internally in actuation spring 330 assists in guiding the actuation spring 330 to prevent it from bending sideways. Guiding element 360 provides at its proximal end a seat portion arranged to act as a seat for supporting the proximal end of actuation spring 330.

The spacer member 400 is formed with stop surfaces 401 positioned a predetermined distance from the distal end of spacer member 400 to cooperate with the rear end 611 of the cartridge 600 to thereby define a precise end of stroke position for the piston 630 inside cartridge 600. As the piston 630, during filling of the cartridge 600, can be accurately positioned with respect to the rear end 611 of the cartridge 600, the exact volume of an expelled dose can be accurately controlled by utilizing the stop surfaces 401 hitting the rear end 611 of cartridge 600 at completion of the expelling operation.

In the embodiment shown, spacer member 400 and a cooperating member associated with the housing may further include one or more pairs of click generating elements such as protrusions adapted to cooperate with click arms to generate click sounds during and/or at the completion of the injection.

As mentioned, in the shown embodiment the actuator in the form of a pre-stressed actuation spring 330 urges the drive ram 310 in the distal direction. In the unactivated state of the injection device 100, a release nut 320 associated with drive ram 310 cooperates with the top housing section 200 and the trigger element 380 to retain the drive ram 310 in an initial axial position against the force of the actuation spring 330. Upon activation of the expelling assembly, i.e. by operating the trigger element, the release 320 nut is released allowing the drive ram to thrust forward for providing a distally directed force on the piston 630.

Alternatively to using a pre-stressed spring which is compressed during manufacture of the device, the device may include a mechanism for compressing the spring as an initial procedure when putting the device into use. Also, the actuator may in other embodiments be formed as a torsion spring which is pre-stressed to exert a torsion force for driving forward a rotational drive of the expelling assembly. Alternatively, the actuator may be in the form of a compressed medium such as a gas. Still alternatively, the actuator may include a gas generator such as an electro-chemical cell.

The drive ram 310 is provided as a deep-drawn metal tube extending along the central longitudinal axis and defining a closed distal end and an open end portion having a collar extending radially outwards at its proximal end. The release nut 320 is arranged at the proximal end of the drive ram 310 to encircle the drive ram 310. Release nut 320 has an axial bore 321 defining a circumferential collar that rests against the collar of the drive ram 310. In this way the release nut 320 prevents the drive ram 310 from moving in the distal direction relative to the release nut 320.

Release nut 320 defines a thread 325 that engages a thread 205 associated with the housing when the device is in the initial state prior to triggering. A releasable lock acts to prevent relative rotation between the release nut 320 and the housing, thereby maintaining the drive ram 310 in the initial axial position.

In the shown embodiment, the lock is provided by the trigger element 380 preventing relative rotation between the release nut 320 and the housing. As shown in FIGS. 5 and 7 axial tracks 386 of trigger element 380 are configured to be engaged by respective axial ribs 206 of top housing section 200 preventing the trigger element from rotation relative to the housing but enabling axial displacement. In the shown embodiment, two radially outwards extending protrusions 328 of release nut 320 are adapted to engage corresponding axial tracks 388 extending radially inwards on an inner surface of trigger element 380 (see FIGS. 5, 6 and 7). The axial tracks 388 each has a limited axial length defining open neighbouring areas at a location at the distal end of axial tracks 386. When sufficient axial displacement of release nut 320 relative to the trigger element 380 occurs, rotation of release nut 320 is enabled. But in the initial state prior to triggering, as long as the trigger element 380 is situated distally relative to a triggering point of the trigger element 380 the release nut 320 is prevented from rotating. The triggering point of the trigger element 380 is located at a point in close proximity but distally to the proximal position of the trigger element 380.

As long as the release nut 320 is prevented from rotating relative to the housing the threaded engagement between the thread 325 of the release nut 320 and the thread 205 of the housing prevents the release nut 320 from being moved axially. Hence, prior to activation of the expelling assembly, the drive ram 310 is also prevented from being moved in the distal direction as long as the trigger element 380 is located distal to the triggering point.

The lead of the threaded connection 325/205 and the dimensions of the engagement between the protrusions 328 and the axial tracks 388 are so configured that, upon displacement of the trigger element 380 towards the triggering point, once the release nut 320 has been released for rotation, the protrusions 328 cannot reengage the axial track 388. Hence, once the expelling assembly has been activated by exerting a force on the needle shield 350 for triggering the device, in case of a potential release in the force exerted on the needle shield, the distal movement of the drive ram 310 cannot be interrupted, i.e. the drive ram 310 will continue its distal movement until the intended end of dose position defined by the elements 401/611.

FIG. 8a shows a partly cut perspective view of the top housing section 200 wherein the trigger element are and the release nut 320 are visible. The release nut, the trigger element and the top housing section together forms a release nut assembly. For clarity, the depicted view only shows selected components of the injection device 100 in the initial state prior to triggering but wherein additional components such as the actuating spring 330 and the drive ram 310 are omitted. The engagement between the thread 325 of the release nut 320 and the thread 325 of the housing is visible. FIG. 8b shows the release nut assembly in a sectional perspective view.

In the following, while mainly referring to FIGS. 1a through 4a, operation of the injection device 100 will be described.

As a first step in operating device 100, the previously mentioned protective cap is removed from the device. As mentioned above, FIGS. 1a and 1b show the device in its initial storage condition but with the protective cap being removed from the housing 200/220. The needle shield 350 is in its extended position whereby the front needle 510 is in a shielded state.

In accordance with the above description, the housing 200/220 acts as an activator relative to the needle shield 350, in that, as the housing is gripped by the hand of the user and the distal end of device 100 is pressed against an injection site, the needle shield 350 will remain arrested relative to the skin and the housing moves distally relative to the needle shield 350 for activating the expelling assembly of the device 100.

As the device 100 is activated the needle shield 350 is moved in a proximal direction relative to lower housing section 220 towards the needle assembly 500. The movement brings the front needle 510 through the small aperture 354 in the needle shield 350. As the needle cannula moves relative to the aperture 354 the above mentioned front cover (not shown) is preferably held back by the geometry around the opening, thereby allowing the front needle 510 to penetrate the front cover while front cover is being compressed between the needle shield 350 and the needle hub 501. Alternatively the front cover could move through the aperture 354 as well. In such case the front cover would be pressed against the patient's skin, thereby being compressed between the device 100 and the injection site. The compression of the front cover can be either in a concertina-like way or be bent sideways, e.g. radially outwards. The front cover may have a specific geometry to ensure that the front cover is always compressed between needle shield 350 and needle hub 501. The aperture 354 in the needle shield 350 could also have a specific geometry for ensuring correct compression of the front cover.

In the state shown in FIGS. 1a and 1b the trigger element 380 is in its distal position due to the pressure exerted by the shield spring 340. The releasable lock that rotationally locks the release nut 320 relative to the housing is enabled and the drive ram 310 is therefore in its initial position. The cartridge 600 is positioned in its proximal storage position.

As the needle shield 350 reaches a predetermined position, i.e. the collapsed position, the needle shield 350 will reach a stop limit, see FIGS. 2a and 2b. In this state the front needle 510 will be inserted in the patient's skin and the front cover (not shown) will be compressed. In accordance with the movement of the needle shield 350, the trigger element 380 has been moved into its proximal position, i.e. past the triggering point.

Cf. to FIG. 8b, as the trigger element 380 has been moved into its proximal position, the axial tracks 388 of trigger element 380 will become displaced so as to disengage from the engagement with the protrusions 328 of release nut 320. This situation is best viewed in FIG. 2a. Due to the actuating spring 330 is exerting a force in the distal direction on drive ram 310 and release nut 320 the threaded engagement 325/205 will induce the release nut 320 to rotate. In FIGS. 2a and 2b, the release nut 320 has been rotated slightly relative to top housing section 200 and, in accordance with the threaded engagement, the release nut 320 and the drive ram 310 have been moved slightly axial towards the distal direction. The initial spacing between the drive ram 310 and the spacing member 400 has been eliminated so that the force of the actuating spring is enabled to act on the piston 630 of cartridge 600 by means of the drive ram 310 and the spacing member 400.

The needle shield 350 and thus the blocking geometry 351 have been moved in the proximal position so that the resilient arms 530 are free to become deflected outwards. As shown in FIGS. 3a and 3b the force from the actuation spring 330 firstly displaces the drive ram 310 and the spacing member 400 and the piston 630 a distance in the distal direction. During the first part of this stage the rear needle 520 is still separated from the septum 620 of the cartridge and the cartridge is thus forced to move with the piston 630. The force of actuating spring 330 is sufficient to overcome the force needed for deflecting the resilient arms 530 outwards. Note however, that in FIGS. 3b and 4b, the resilient arms 530 are shown superposed relative to the wall sections of the cartridge 600. A more correct depiction of how the resilient arms 530 are actually deflected would depict the resilient arms having been deflected outwards to lie against the outer cylindrical surface of the cartridge 600.

Initially, as the cartridge 600 moves distally, the distance between the stop surface 401 of the spacer element 400 and the rear end 611 of the cartridge 600 remains unchanged as the piston 630 generally does not move relative to the body of the cartridge 600. However, after the cartridge 600 has been moved fully in the distal direction, the piston 630 begins its movement inside cartridge 600, the said distance decreases.

At some point the cartridge 600 is moved fully into its distal active position where it meets a stop feature formed in the needle hub 501. The rear needle 620 has penetrated the septum 620 of the cartridge and fluid communication between the needle cannula and the medicament contained in the cartridge 600 has been enabled. In this position the needle cannula is in contact with both the patient's skin and the medicament contained in the cartridge 600. After fluid communication between needle cannula and cartridge 600 is established the medicament is injected into the patient by means of the drive ram 310 being now forced relative to top housing section 200 and being urged distally by actuating spring 330. In the state shown in FIGS. 3a and 3b, the force exerted by the actuating spring 330 has acted on the drive ram 310 for expelling a first portion of the fluid from the cartridge 600.

The actuating spring 330 continues to act on the piston 630 advancing the piston to a predefined end of dose position determined by the end of dose feature. When the stop surface 401 of spacer element 400 reaches the rear end 611 of the cartridge 600 the movement of the drive ram 310 is stopped, thereby stopping the expelling of the medicament (cf. FIG. 4b).

FIGS. 4a and 4b shows the injection the device 100 after it has been retracted relative to the injection site. As the device is removed the needle shield 350 is moved forward relative to the lower housing section 220, the needle shield being urged by means of the shield spring 340, thereby releasing the compressive pressure on the front cover (not shown). As the needle shield 350 no longer holds the front cover in a collapsed position the front cover will tend to return to its extended position covering the front needle 510. In alternative embodiments, the front cover could remain in its collapsed position.

As the device 100 is removed from the patient the front needle 510 is removed from the skin of the patient. In embodiments where said front cover returns to its extended position, the front cover will prevent excess medicament that is expelled from the needle cannula from dripping out of the device. The rear cover (also not shown) remains in its collapsed position due to the pressure from the cartridge 600.

The needle shield 350 may include a lock which renders the needle shield 350 locked against proximal movements once it has been returned from the proximal collapsed position to the distal extended position, i.e. where the front needle 510 is in its shielded state.

In accordance with a first type of autoinjector described above, a trigger principle has been described wherein a plunger includes a plunger thread that is in engagement with a base thread. The plunger is maintained in pre-triggering state by means of the threaded connection wherein relative rotation is prevented. Upon being triggered, the plunger thread and the base thread are allowed to rotate relative to each other ultimately allowing the plunger to move in a distal direction.

In accordance with the general principle, in a second type of autoinjector, the above described trigger principle may be used in an alternative autoinjector which is slightly modified relative to the first type autoinjector. The modifications mainly rely in that the release nut of the plunger may be prevented from being rotated both during storage and during operation of the autoinjector. Instead the base thread may be arranged on a rotatable component which during storage is prevented from rotating relative to the housing. The rotatable component of the injector is rotatably mounted relative to the housing but may be prevented from moving axially relative to the housing. Subsequent to triggering, the rotatable component is allowed to rotate relative to the release nut in accordance with the threaded connection between the base thread component and the plunger thread component.

Reference is made to FIG. 9, which shows the basic components needed for such a second type autoinjector. Comparing FIG. 8b and FIG. 9, the above described embodiments are modified in defining a rotatable component 1204 which is rotatably mounted relative to the housing 1200 but prevented from moving axially. The rotatable component 1204 defines a base thread component 1205. The release nut 1320 defines a plunger thread component 1325 adapted to initially engage the base thread component 1205. The release nut 1320 is prevented from rotating relative to the housing. The means for preventing said rotation may for example be provided by forming an axial track 1321 of the release nut 1320 that engages a not shown geometry of the drive ram. The drive ram may be made non-rotatable by forming appropriate rotational locks between the drive ram, the spacing member and the housing.

In the embodiment shown in FIG. 9, the trigger element 1380 is prevented from rotating relative to the housing 1200. The trigger element and the rotatable component define respective cooperating lock geometries 1388, 1208 configured to, prior to triggering, maintain a rotational lock between the rotatable component and the housing. The rotatable component 1204 is biased in an expelling rotational direction by being urged by the actuating spring. When the trigger element 1380 assumes its initial extended position, the cooperating lock geometries 1388, 1208 engage to thereby prevent the rotatable component 1204 from rotating in the expelling rotational direction. When the autoinjector is to be triggered, the trigger element 1380 is pushed proximally towards its triggering position. This displaces the cooperating lock geometries 1388, 1208 relative to each other. Due to threaded engagement between threads 1325/1205, the force emanating from the actuating spring will tend to rotate the rotatable component 1204. Once the trigger element 1380 has been moved proximally relative to the triggering position, rotation of the rotatable component 1204 is now allowed due to the cooperating lock geometries 1388, 1208 become disengaged.

Some preferred embodiments have been shown in the foregoing, but it should be stressed that the invention is not limited to these, but may be embodied in other ways within the subject matter defined in the following claims.

The invention claimed is:

1. An autoinjector for expelling a single dose of drug from a drug cartridge, the autoinjector comprising:
   a base forming a housing,
   a needle that is fixedly mounted relative to the base and comprising a front needle;
   the drug cartridge arranged relative to the base, the drug cartridge comprising:
      an elongated body having a distal end and a proximal end and defining a central longitudinal axis, the body having a distally arranged outlet adapted for connection to the needle, and
      a piston accommodated in the body, the piston configured for being driven axially in a distal direction to expel the dose of the drug through the outlet,
   a plunger adapted for cooperation with the piston,
   an actuating spring provided as a helical compression spring arranged to act on the plunger by exerting an axial force on the plunger to drive the piston distally,
   a needle shield axially movable relative to the base between an extended position and a collapsed position,
   wherein the autoinjector defines a lock configured for releasably maintaining the plunger in an initial axial position where the actuating spring is strained, the lock being operated by the needle shield, wherein manual operation of the needle shield by movement of the needle shield relative to the front needle towards the collapsed position causes manual penetration of the front needle into an injection site and causes subsequent release of the lock,
   wherein the plunger defines a plunger thread and the base defines a base thread fixedly associated with the base, wherein the base thread is adapted to cooperate with the plunger thread,
   wherein prior to activation, the plunger thread engages the base thread and the lock acts to prevent relative rotation between the plunger and the base, thereby maintaining the plunger in an initial axial position,
   wherein, upon the needle shield being moved towards the collapsed position, the lock is released to enable the force exerted by the actuating spring to cause relative rotation between the plunger and the base causing release of the plunger from the initial axial position and expelling the dose of the drug, and
   wherein the plunger thread is engaged with the housing by engaging the base thread during an initial first axial displacement of the plunger and where the plunger thread is released from engagement with the housing by releasing engagement with the base thread allowing the plunger to subsequently continue axial displacement in a second axial displacement.

2. The autoinjector as defined in claim 1, wherein a needle shield spring biases the needle shield towards the extended position.

3. The autoinjector as defined in claim 2, wherein the needle shield spring is an element separate from the actuating spring.

4. The autoinjector as defined in claim 1, wherein the lock includes a first lock element that is axially movable as the needle shield moves from the extended position towards the collapsed position, wherein the first lock element and the plunger define respective cooperating lock geometries configured to, prior to activation, maintain a rotational lock between the plunger and the base, the cooperating lock geometries being adapted to unlock to enable rotation between the plunger and the base upon the needle shield being moved towards the collapsed position.

5. The autoinjector as defined as in claim 4, wherein the first lock element is prevented from rotating relative to the base and wherein the first lock element and the plunger define the respective cooperating lock geometries configured to, prior to activation, maintain the rotational lock between the plunger and the first lock element, the cooperating lock geometries being adapted to unlock to enable rotation between the plunger and the first lock element as the needle shield is moved towards the collapsed position.

6. The autoinjector as defined in claim 1, wherein an external diameter of the plunger thread is larger than an internal diameter of a cylindrical section of the body of the cartridge.

7. The autoinjector as defined in claim 1, wherein the plunger thread is accommodated at a proximal end of the plunger.

8. The autoinjector as defined in claim 1, wherein the helical compression spring is arranged internally in a longitudinal bore of the plunger.

9. The autoinjector as defined in claim 1, wherein the autoinjector irreplaceably accommodates the drug cartridge within the base and wherein the drug cartridge cannot be removed from the autoinjector without the use of tools.

10. The autoinjector as defined in claim 1, wherein the force acting for causing rotation between the plunger and the base for releasing the plunger from the initial axial position is at least partly exerted by the actuating spring.

11. The autoinjector as defined in claim 10, wherein the force acting for causing rotation between the plunger and the base for releasing the plunger and the base from the initial axial position is exclusively exerted by the actuating spring.

* * * * *